US00PP26704P3

(12) United States Plant Patent
Zary

(10) Patent No.: US PP26,704 P3
(45) Date of Patent: May 10, 2016

(54) HYBRID TEA ROSE PLANT NAMES 'JACIBEGO'

(50) Latin Name: *Rosa hybrida*
Varietal Denomination: JACibego

(71) Applicant: J & P PARK ACQUISITIONS, INC., Columbia, SC (US)

(72) Inventor: Keith Zary, Troy, OH (US)

(73) Assignee: J & P PARK ACQUISITIONS, INC., Columbia, SC (US)

( * ) Notice: Subject to any disclaimer, the term of this patent is extended or adjusted under 35 U.S.C. 154(b) by 128 days.

(21) Appl. No.: 13/998,638

(22) Filed: Nov. 19, 2013

(65) Prior Publication Data

US 2015/0143592 P1 May 21, 2015

(51) Int. Cl.
*A01H 5/02* (2006.01)

(52) U.S. Cl.
USPC ..... Plt./137

(58) Field of Classification Search
USPC ..... Plt./133, 137
See application file for complete search history.

(56) References Cited

U.S. PATENT DOCUMENTS

PP8,279 P 6/1993 McGredy, IV
PP19,107 P2 8/2008 Zary

*Primary Examiner* — Keith Robinson
(74) *Attorney, Agent, or Firm* — McKee, Voorhees & Sease, PLC

(57) ABSTRACT

A new variety of Hybrid Tea rose suitable for garden decoration, having flowers white in coloration.

1 Drawing Sheet

Classification: The present invention relates to a new *Rosa hybrida* plant.

Variety denomination: The new plant has the varietal denomination 'JACibego".

BACKGROUND OF THE INVENTION

This invention relates to a new and distinct variety of Hybrid Tea Rose. It has as its seed parent the variety known as 'JP 4597', a seedling Red Hybrid Tea rose that was never patented and as the pollen parent 'MACgenev' (U.S. Plant Pat. No. 8,279).

SUMMARY OF THE INVENTION

Among the features which distinguish the new variety from other presently available and commercial rose cultivars known to the inventor are the following combinations of characteristics, an attractive white flower with a very pale pink blush, strong upright and vigorous growth habit, long straight stems for cutting, moderate vase life, an excellent high centered flower form and a very strong sweet fruity fragrance. The plant has a bushy upright growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'JACibego' may be asexually propagated by cuttings, budding and grafting. The budding and grafting successfully occurred on the plant/rootstock *Rosa hybrida* cv. 'Dr. Huey' (not patented). The most vigorous plants are produced by budding.

COMPARISON WITH PARENTS

The new rose may be distinguished from its seed parent, 'JP 4597' by the following combination of characteristics:

whereas 'JP 4597' bears flowers that are a deep red color, 'JACibego' has flowers that are mostly white in color. 'JP 4597' is also a taller hybrid tea ranging from 150 to 180 cm. in height while 'JACibego' is 120 to 150 cm. in height. 'JP 4597' also has little fragrance while 'JACibego' is strongly fragrant.

The new variety may be distinguished from its pollen parent, 'MACgenev' by being much lighter in color. 'JACibego' is mostly white while 'MACgenev' is creamy pink. 'MACgenev' has a few more petals than 'JACibego'. The new variety is classified as a Hybrid Tea rose with a bushy upright growing habit.

COMPARISON WITH THE CLOSEST COMMERCIALLY AVAILABLE CULTIVAR

The new variety may be distinguished from its closest commercially available cultivar, 'JACsegra' (U.S. Plant Pat. No. 19,107) by the following combination of characteristics: whereas 'JACsegra' bears double flowers with 45 or more petals, 'JACibego' bears double flowers with 25-30 petals. The new variety has a bushy upright growing habit (about 120 to 140 cm. in height), whereas the closest commercially available cultivar has a bushy upright habit and is significantly taller(about 150 to 180 cm in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Tipp City, Ohio in the month of July. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Tipp City, Ohio in the month of July. Phenotypic expression may vary with environmental, cultural and climatic conditions, as well as differences in conditions of light and soil.

FLOWER

The new variety bears medium to large sizes blooms borne singly or is very small clusters of three flowers. Flowers are borne on strong medium length stems 40 to 60 cm in length and 9-10 mm in diameter. The flower shape is high centered. Outdoors, the plant blooms abundantly and nearly continuously during the growing season. The number of flowers grown on a well-established three year old rose~averages 11 to 15 flowers in the growing season. The flowers have only a very strong sweet fruity fragrance.

BUD

The bud is about 4.0 to 5.0 cm. long and about 3.5 cm. in diameter when the petals start to unfurl. The bud is long and pointed ovoid in shape. As the petals open (after the calyx breaks), the bud is about 5.0 to 5.5 cm. in diameter at the widest point, about 5.0 to 5.5 cm. in length, and moderately globose in form. When the sepals first divide, the bud color is 155D with a faint blush of N155C. When half blown, the upper sides of the petals are 155D in color except toward the center of the flower where it is N155C and the lower sides of the petals are 155D.

The sepals are 25-30 mm. in length and about 10-11 mm. in width at the widest point. The color of the sepal is 138B on the upper surface and 146C on the lower surface. The outer surface of the sepal is smooth and bears from 0 to 8 foliaceous appendages. The inner surface of the sepal is covered with fine wooly tomentum; sepal margins are lined with many glands and hairs.

The peduncle is stiff and erect, medium in length (about 6.0-8.0 cm.), and of average caliper (about 5 mm. in diameter). It is smooth with only a very few glands. Peduncle color is 146B. The strength of the peduncle is strong. The receptacle of the flower is funnel shaped and medium in size (about 10 mm. in length and about 8 mm. in diameter). Its surface is smooth with only an occasional gland. The receptacle color is 146C.

BLOOM

When fully open, the bloom ranges from about 10 cm.-13 cm. in diameter with the largest flowers expressed under cool night time temperatures. Petalage is double with about 30 petals under normal conditions. When first open, the bloom form is very high centered and the petals are imbricated with petal edges somewhat reflexed outward. The bloom flattens out somewhat over time as the flowers opens.

PETALS

The substance of the petals is thick and leathery with a smooth surface. The petals are about 5.0 to 6.0 cm. in length and about 4.5 to 5.5 cm. in width at the widest point. The shape of the petals is orbiculate and flat with rounded apices. The petal density is dense. Petal margins are entire. Petals are arranged in an imbricated fashion and drop off of the plant cleanly before dying. Petals last on the plant for about 5 days. As a cut flower the petals last about 7 days.

Petaloids number from 2 to 5 and are N155D in color. Petaloids are about 1.5 cm to 3.5 cm. in length and about 1.5 to about 2.5 cm. in width at the widest point. Petaloids are irregularly shaped somewhat obovate to oblanceolate with rounded apices.

NEWLY OPENED FLOWER

The upper side of the petals is 155D in color on the newly opened flower. The reverse side of the petals is 155D in color. The base of the petals has a color spot of about 0.5 cm. to 0.6 cm by about 10 mm. with a color of 1D. The under and upper surface colors of the petaloids are similar in coloration to the upper and under surfaces of the petals in the center of the flower.

The general tonality at the end of the first day is no change.

THREE-DAY-OLD FLOWER

At the end of the third day the tonality is generally unchanged. By day 5 the color of the petals is little changed. The under and upper surface colors of the petaloids are similar in coloration to the upper and under surfaces of the petals.

MALE REPRODUCTIVE ORGANS

Stamens average about 50 to 60 in number and are about 6.0 to 7.0 mm. in length. Anthers are 0.3 cm. in length with color of 19D. Anthers are arranged regularly around the styles and mixed with petaloids.

Filaments are of average length (about 3 to 4 mm) and are 158C in color. Pollen is sparse and is 22A in color.

FEMALE REPRODUCTIVE ORGANS

Pistils vary in number (average about 50). Styles are moderately even, average in length (about 4 mm.) moderately heavy in caliper, and bunched. Style color is 184A.

Stigmas are 182D in color and 1.0 mm in length. Ovaries are usually all enclosed in the calyx.

Hips have not been observed on this variety when grown in Tipp City, Ohio.

FOLIAGE

The compound leaves are usually comprised of three to seven leaflets and are borne abundantly. The five-leaflet leaves are about 10 cm. long and 7 cm. wide.

The terminal leaflets are pointed oval in shape. The base is rounded oblique in shape and the apex shape is acuminate. The upper side of the leaves is leathery and matte with a single serrated edge. The terminal leaflets are about 5.0 to about 5.5 cm. in length and about 3.0 cm. in width at the widest point.

New foliage is 185A in color on the upper side and 185B in color on the under-side. Old foliage is 139A on the upper side and N138B on the under-side.

The vein color of the leaves is 138B and the venation patter is reticulate.

The rachis is average in caliper and rough. The rachis length averages 9 cm. The upper side is shallowly grooved with many hairs and few stipitate glands on the edges of the grooves. The underside of the rachis is rough with some hairs and few small prickles. The rachis color is 138B.

The stipules are about 8 to 10 mm. in length and about 4 mm. in width. They have serrated edges. The auricle is subulate in shape. The stipules color is 138B. The petiole is average in caliper and rough. The upper side is shallowly grooved with many hairs and few stipitate glands on the edges of the grooves. The underside of the petiole is rough with some hairs and few small prickles. The petiole is about 7.0 to about 9 mm. in length and about 0.1 to about 0.2 cm in width at the widest point. The strength of the petiole is strong. The petiole color is 138B.

The plants root type is fibrous. The root color is Grey-Brown N199B. At 76° F. (24° C.) root zone temperature and 95% humidity, the soft wood cutting stuck in well drained potting soil with 3000 ppm Hormex brand rooting hormone will root in 14 days from sticking. At 56 days from sticking, the rooted cutting is strong enough to plant in the field.

The plant displays an above average degree of resistance to rust (*Phragmidium* spp.) and powdery mildew (*Sphaerotheca pannosa* var. *rosae*) and is susceptible to black spot (*Diplocarpon rosae*) as compared to other commercial varieties grown under comparable conditions in Tipp City, Ohio. 'JACibego' is cold hardy without protection through zone 6 and is winter hardy in zone 5 with protection.

GROWTH

The plant has a bushy upright growing habit (about 120 to 130 cm. in height and about 100 to 120 cm. spread at the widest point), with full branching. It displays vigorous growth and the canes are strong (about 1.5 to about 2.0 cm. in diameter at the widest point). Anthocyanin coloration of the young shoot is present with medium intensity. Stems of new wood are 137A in color. Stems of old wood are 136B in color. The new wood and the old wood bear some large prickles. The Prickles are moderately hooked downward with a short narrow oval base. Prickles are of 6 to 8 mm. in length. Young prickles are 183C in color. When mature, prickles are 200C in color. On average, there are 7-9 prickles per 15 centimeters of rose stem.

There are no small prickles on the main stalk or lateral stalks.

I claim:

1. A new and distinct Hybrid Tea rose plant of the variety substantially as described and illustrated herein.

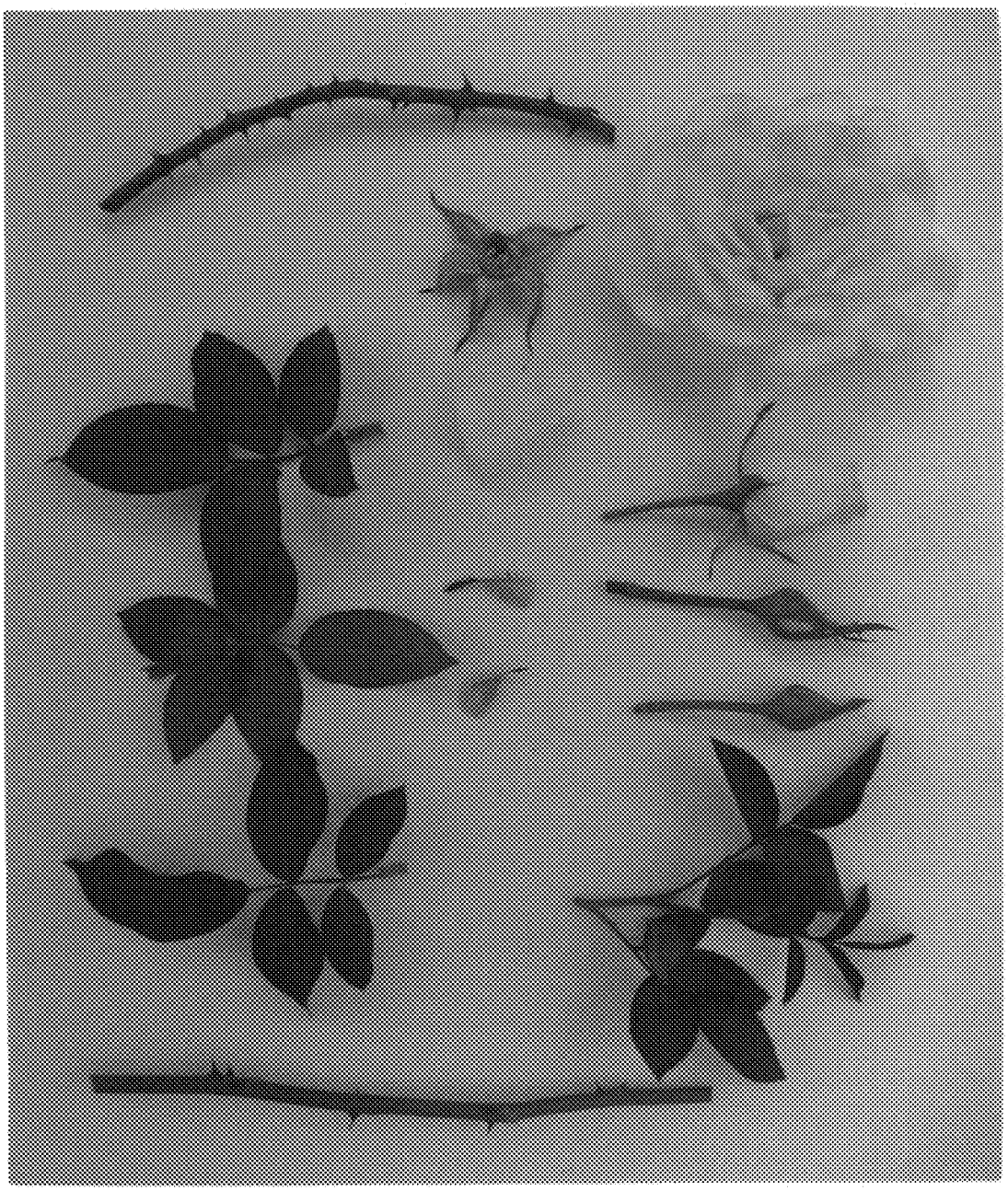

* * * * *